US010562952B2

United States Patent
Mackall et al.

(10) Patent No.: US 10,562,952 B2
(45) Date of Patent: Feb. 18, 2020

(54) ANTI-CD276 CHIMERIC ANTIGEN RECEPTORS

(71) Applicant: The United States of America, as represented by the Secretary, Department of Health and Human Services, Bethesda, MD (US)

(72) Inventors: Crystal L. Mackall, Stanford, CA (US); Yongzhi Karen Cui, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/757,728

(22) PCT Filed: Sep. 9, 2016

(86) PCT No.: PCT/US2016/050887
§ 371 (c)(1),
(2) Date: Mar. 6, 2018

(87) PCT Pub. No.: WO2017/044699
PCT Pub. Date: Mar. 16, 2017

(65) Prior Publication Data
US 2018/0346544 A1    Dec. 6, 2018

Related U.S. Application Data

(60) Provisional application No. 62/216,447, filed on Sep. 10, 2015.

(51) Int. Cl.
| C07K 14/705 | (2006.01) |
| A61P 35/00 | (2006.01) |
| G01N 33/574 | (2006.01) |

(52) U.S. Cl.
CPC ........ C07K 14/70532 (2013.01); A61P 35/00 (2018.01); G01N 33/574 (2013.01); C07K 2319/02 (2013.01); C07K 2319/03 (2013.01)

(58) Field of Classification Search
CPC .......... C07K 14/70532; C07K 2319/02; C07K 2319/03; A61P 35/00; G01N 33/574
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 8,802,091 B2 | 8/2014 | Johnson et al. |
| 2012/0244133 A1 | 9/2012 | Rosenberg et al. |
| 2013/0149236 A1 * | 6/2013 | Johnson .................. A61K 45/06 424/1.11 |
| 2014/0274909 A1 * | 9/2014 | Orentas .............. C07K 16/2803 514/19.3 |

FOREIGN PATENT DOCUMENTS

| WO | WO 2011/109400 A2 | 9/2011 | |
| WO | WO-2013059593 A1 * | 4/2013 | ......... C07K 16/2803 |
| WO | WO 2014/065961 A1 | 5/2014 | |
| WO | WO 2014/160627 A1 | 10/2014 | |

OTHER PUBLICATIONS

Clay et al., "Efficient Transfer of a Tumor Antigen-Reactive TCR to Human Peripheral Blood Lymphocytes Confers Anti-Tumor Reactivity," *J. Immunol.*, 163(1): 507-513 (1999).
Dudley et al., "Generation of tumor-infiltrating lymphocyte cultures for use in adoptive transfer therapy for melanoma patients," *J. Immunother.*, 26: 332-42 (2003).
International Bureau, International Search Report and Written Opinion in International Application No. PCT/US2016/050887, dated Dec. 1, 2016.
Loo et al., "Development of an Fc-Enhanced Anti-B7-H3 Monoclonal Antibody with Potent Antitumor Activity," *Clin Cancer Res.*, 18(14): 3834-45 (2012).
Orentas et al., "Identification of Cell Surface Proteins as Potential Immunotherapy Targets in 12 Pediatric Cancers," *Frontiers in Oncol.*, 2(1): 1-16 (2012).
Riddell et al., "The use of anti-CD3 and anti-CD28 monoclonal antibodies to clone and expand human antigen-specific T cells," *J. Immunol. Methods*, 128: 189-201 (1990).
Sadelain et al., "The promise and potential pitfalls of chimeric antigen receptors," *Curr. Opin. Immunol.*, 21: 215-223 (2009).
Zhao et al., "Primary human lymphocytes transduced with NY-ESO-1 antigen-specific TCR genes recognize and kill diverse human tumor cell lines," *J. Immunol.*, 174: 4415-4423 (2005).

* cited by examiner

*Primary Examiner* — Karlheinz R. Skowronek
*Assistant Examiner* — Li N Komatsu
(74) *Attorney, Agent, or Firm* — Leydig, Voit & Mayer, Ltd.

(57) ABSTRACT

Chimeric antigen receptors (CARs) that specifically bind to and immunologically recognize CD276 are disclosed. Related nucleic acids, recombinant expression vectors, host cells, populations of cells, and pharmaceutical compositions relating to the polypeptides and proteins are also disclosed. Methods of detecting the presence of cancer in a mammal and methods of treating or preventing cancer in a mammal are also disclosed.

8 Claims, 9 Drawing Sheets
Specification includes a Sequence Listing.

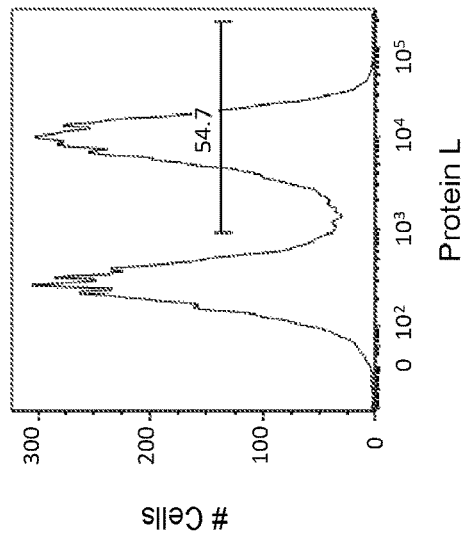
FIG. 2A
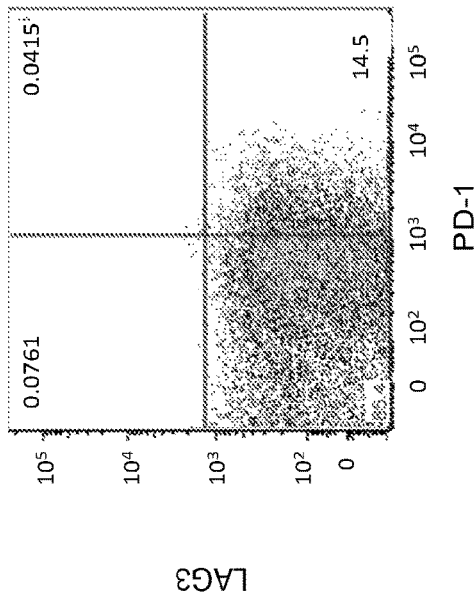
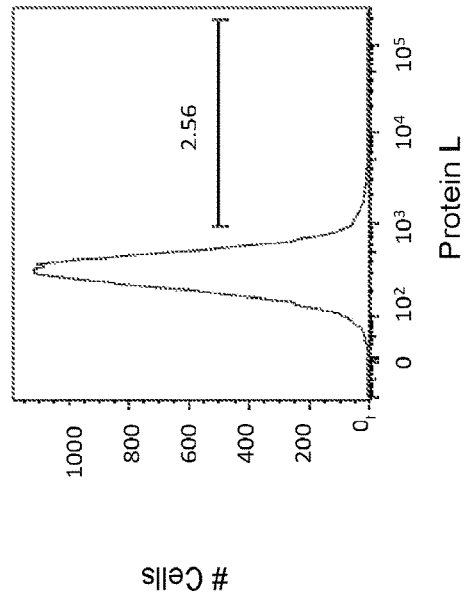
FIG. 2B
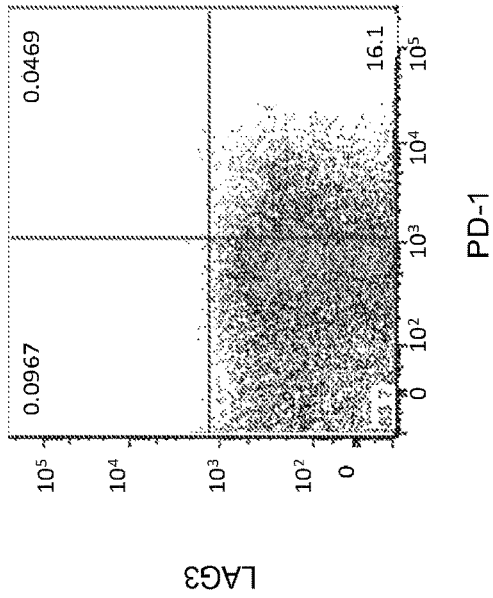

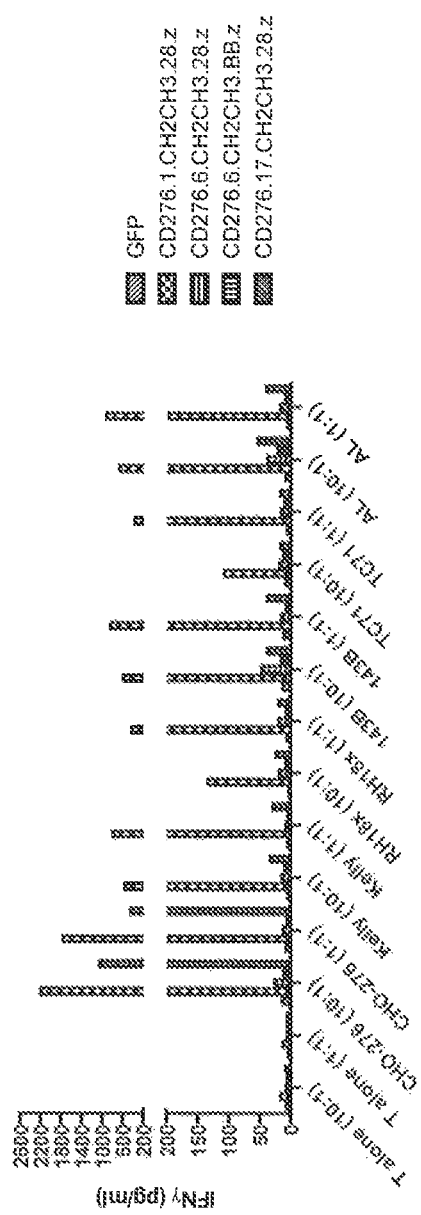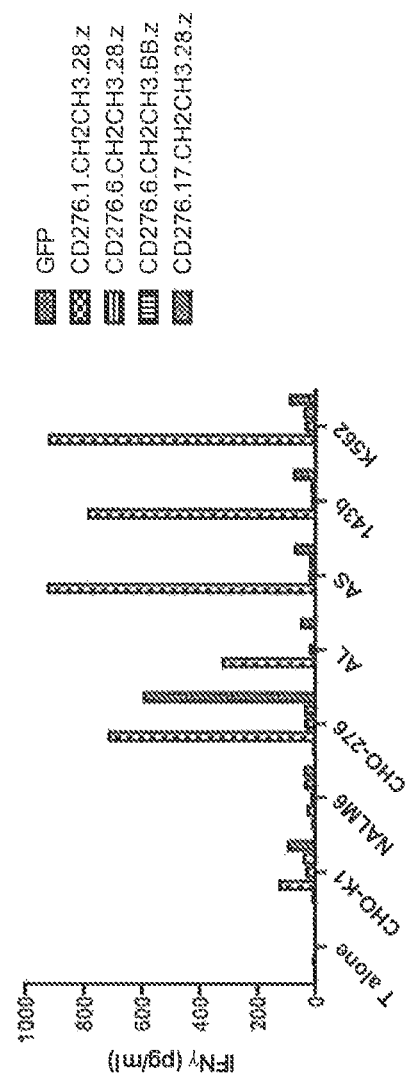
FIG. 4A
FIG. 4B

SEQUENCE LISTING

```
<160> NUMBER OF SEQ ID NOS: 21

<210> SEQ ID NO 1
<211> LENGTH: 8
<212> TYPE: PRT
<213> ORGANISM: Mus musculus

<400> SEQUENCE: 1

Gly Phe Thr Phe Ser Ser Phe Gly
1               5

<210> SEQ ID NO 2
<211> LENGTH: 8
<212> TYPE: PRT
<213> ORGANISM: Mus musculus

<400> SEQUENCE: 2

Ile Ser Ser Asp Ser Ser Ala Ile
1               5

<210> SEQ ID NO 3
<211> LENGTH: 16
<212> TYPE: PRT
<213> ORGANISM: Mus musculus

<400> SEQUENCE: 3

Gly Arg Gly Arg Glu Asn Ile Tyr Tyr Gly Ser Arg Leu Asp Tyr Trp
1               5                   10                  15

<210> SEQ ID NO 4
<211> LENGTH: 6
<212> TYPE: PRT
<213> ORGANISM: Mus musculus
```

```
<400> SEQUENCE: 4

Gln Asn Val Asp Thr Asn
1               5

<210> SEQ ID NO 5
<211> LENGTH: 4
<212> TYPE: PRT
<213> ORGANISM: Mus musculus

<400> SEQUENCE: 5

Ser Ala Ser Tyr
1

<210> SEQ ID NO 6
<211> LENGTH: 9
<212> TYPE: PRT
<213> ORGANISM: Mus musculus

<400> SEQUENCE: 6

Gln Gln Tyr Asn Asn Tyr Pro Phe Thr
1               5

<210> SEQ ID NO 7
<211> LENGTH: 120
<212> TYPE: PRT
<213> ORGANISM: Mus musculus

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Asp Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val
        115                 120

<210> SEQ ID NO 8
<211> LENGTH: 107
<212> TYPE: PRT
<213> ORGANISM: Mus musculus

<400> SEQUENCE: 8

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
                20                  25                  30

Val Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 9
<211> LENGTH: 69
<212> TYPE: PRT
<213> ORGANISM: Artificial sequence
<220> FEATURE:
<223> OTHER INFORMATION: synthetic

<400> SEQUENCE: 9

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
                35                  40                  45

Trp Ala Pro Leu Ala Gly Thr Cys Gly Val Leu Leu Leu Ser Leu Val
50                  55                  60

Ile Thr Leu Tyr Cys
65

<210> SEQ ID NO 10
<211> LENGTH: 42
<212> TYPE: PRT
<213> ORGANISM: Artificial sequence
<220> FEATURE:
<223> OTHER INFORMATION: synthetic

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
                35                  40

<210> SEQ ID NO 11
<211> LENGTH: 112
<212> TYPE: PRT
<213> ORGANISM: Artificial sequence
<220> FEATURE:
<223> OTHER INFORMATION: synthetic

<400> SEQUENCE: 11

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

```
Arg Arg Gly Lys Gly His Asp Gly Leu Tyr Gln Gly Leu Ser Thr Ala
             85                  90                  95

Thr Lys Asp Thr Tyr Asp Ala Leu His Met Gln Ala Leu Pro Pro Arg
            100                 105                 110

<210> SEQ ID NO 12
<211> LENGTH: 496
<212> TYPE: PRT
<213> ORGANISM: Artificial sequence
<220> FEATURE:
<223> OTHER INFORMATION: synthetic

<400> SEQUENCE: 12

Met Val Ala Thr Leu Leu Val Thr Ser Leu Leu Leu Cys Glu Leu Pro
1               5                  10                  15

His Pro Ala Phe Leu Leu Ile Pro Asp Thr Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Thr Phe Ser Ser Phe Gly Met His Trp Val Arg
    50                  55                  60

Gln Ala Pro Gly Lys Gly Leu Glu Trp Val Ala Tyr Ile Ser Ser Asp
65                  70                  75                  80

Ser Ser Ala Ile Tyr Tyr Ala Asp Thr Val Lys Gly Arg Phe Thr Ile
                85                  90                  95

Ser Arg Asp Asn Ala Lys Asn Ser Leu Tyr Leu Gln Met Asn Ser Leu
            100                 105                 110

Arg Asp Glu Asp Thr Ala Val Tyr Tyr Cys Gly Arg Gly Arg Glu Asn
            115                 120                 125

Ile Tyr Tyr Gly Ser Arg Leu Asp Tyr Trp Gly Gln Gly Thr Thr Val
        130                 135                 140

Thr Val Ser Ser Gly Gly Gly Ser Gly Gly Gly Ser Gly Gly Gly Gly
145                 150                 155                 160

Gly Gly Ser Asp Ile Gln Leu Thr Gln Ser Pro Ser Phe Leu Ser Ala
            165                 170                 175

Ser Val Gly Asp Arg Val Thr Ile Thr Cys Lys Ala Ser Gln Asn Val
            180                 185                 190

Asp Thr Asn Val Ala Trp Tyr Gln Gln Lys Pro Gly Lys Ala Pro Lys
            195                 200                 205

Ala Leu Ile Tyr Ser Ala Ser Tyr Arg Tyr Ser Gly Val Pro Ser Arg
        210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys Gln Gln Tyr Asn Asn
            245                 250                 255

Tyr Pro Phe Thr Phe Gly Gln Gly Thr Lys Leu Glu Ile Lys Ala Ala
            260                 265                 270

Ala Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
            325                 330                 335
```

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
        420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
        450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
            485                 490                 495

<210> SEQ ID NO 13
<211> LENGTH: 26
<212> TYPE: PRT
<213> ORGANISM: Artificial sequence
<220> FEATURE:
<223> OTHER INFORMATION: synthetic

<400> SEQUENCE: 13

Met Val Ala Thr Leu Leu Val Thr Ser Leu Leu Leu Cys Glu Leu Pro
1               5                   10                  15

His Pro Ala Phe Leu Leu Ile Pro Asp Thr
            20                  25

<210> SEQ ID NO 14
<211> LENGTH: 17
<212> TYPE: PRT
<213> ORGANISM: Artificial sequence
<220> FEATURE:
<223> OTHER INFORMATION: synthetic

<400> SEQUENCE: 14

Ser Ser Gly Gly Gly Gly Ser Gly Gly Gly Gly Ser Gly Gly Gly Gly
1               5                   10                  15

Ser

<210> SEQ ID NO 15
<211> LENGTH: 65
<212> TYPE: PRT
<213> ORGANISM: Artificial sequence
<220> FEATURE:
<223> OTHER INFORMATION: synthetic

<400> SEQUENCE: 15

Val Met Tyr Pro Pro Pro Tyr Leu Asp Asn Glu Lys Ser Asn Gly Thr
1               5                   10                  15

Ile Ile His Val Lys Gly Lys His Leu Cys Pro Ser Pro Leu Phe Pro
            20                  25                  30

Gly Pro Ser Lys Pro Phe Trp Val Leu Val Val Val Gly Gly Val Leu
        35                  40                  45

```
Ala Cys Tyr Ser Leu Leu Val Thr Val Ala Phe Ile Ile Phe Trp Val
        50                  55                  60
Arg
65

<210> SEQ ID NO 16
<211> LENGTH: 84
<212> TYPE: PRT
<213> ORGANISM: Artificial sequence
<220> FEATURE:
<223> OTHER INFORMATION: synthetic

<400> SEQUENCE: 16

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 17
<211> LENGTH: 40
<212> TYPE: PRT
<213> ORGANISM: Artificial sequence
<220> FEATURE:
<223> OTHER INFORMATION: synthetic

<400> SEQUENCE: 17

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 18
<211> LENGTH: 47
<212> TYPE: PRT
<213> ORGANISM: Artificial sequence
<220> FEATURE:
<223> OTHER INFORMATION: synthetic

<400> SEQUENCE: 18

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 19
<211> LENGTH: 1491
<212> TYPE: DNA
<213> ORGANISM: Artificial sequence
<220> FEATURE:
<223> OTHER INFORMATION: synthetic
```

<400> SEQUENCE: 19

```
atggttgcca ccctgctcgt gacaagcctg ctgctgtgcg agctgcccca ccctgccttt      60
ctgctgatcc ccgataccga ggtgcagctg gtggaatctg gcggcggact ggtgcagcct     120
ggcggatctc tgagactgag ctgtgccgcc agcggcttca ccttcagcag cttcggaatg     180
cactgggtgc gccaggcccc tggcaaagga ctggaatggg tggcctacat cagcagcgac     240
agcagcgcca tctactacgc cgacaccgtg aagggccggt tcaccatctc ccggacaaac     300
gccaagaaca ccctgtacct gcagatgaac tccctgcggg acgaggacac cgccgtgtac     360
tattgcggca gaggcagaga gaacatctat acggcagca gactggacta ctggggccag      420
ggcacaaccg tgacagtgtc tagcggaggc ggaggatcag gcggcggagg aagtggcgga     480
ggggatctg atatccagct gacccagagc cccagcttcc tgagcgcctc tgtgggcgac      540
agagtgacca tcacatgcaa ggccagccag aacgtggaca ccaacgtggc ctggtatcag     600
cagaagcccg gcaaggcccc taaggccctg atctacagcg ccagctaccg gtacagcggc     660
gtgcccagca gattttctgg cagcggctcc ggcaccgact tcaccctgac aatcagcagc     720
ctgcagcccg aggacttcgc cacctactac tgccagcagt acaacaacta cccctttcacc    780
ttcggccagg gaaccaagct ggaaatcaaa gcggccgcaa ccacgacgcc agcgccgcga     840
ccaccaacac cggcgcccac catcgcgtcg cagcccctgt ccctgcgccc agaggcgtgc     900
cggcagcgc ggggggcgc agtgcacacg aggggctgg acttcgcctg tgatatctac        960
atctgggcgc ccttggccgg acttgtgggg gtccttctcc tgtcactggt tatcaccctt     1020
tactgcaaac ggggcagaaa gaaactcctg tatatattca acaaccatt tatgagacca     1080
gtacaaacta ctcaagagga agatggctgt agctgccgat ttccagaaga agaagaagga     1140
ggatgtgaac tgagagtgaa gttcagcagg agcgcagacg ccccccgcgta ccagcagggc     1200
cagaaccagc tctataacga gctcaatcta ggacgaagag aggagtacga tgtttttggac     1260
aagagacgtg gccgggaccc tgagatgggg ggaaagccga aaggaagaa ccctcaggaa      1320
ggcctgtaca atgaactgca gaaagataag atggcggagg cctacagtga gattgggatg     1380
aaaggcgagc gccggagggg caaggggcac gatggccttt accagggtct cagtacagcc     1440
accaaggaca cctacgacgc ccttcacatg caggccctgc cccctcgcta a              1491
```

<210> SEQ ID NO 20
<211> LENGTH: 223
<212> TYPE: PRT
<213> ORGANISM: Artificial sequence
<220> FEATURE:
<223> OTHER INFORMATION: synthetic

<400> SEQUENCE: 20

```
Thr Thr Thr Pro Ala Pro Arg Pro Pro Thr Pro Ala Pro Thr Ile Ala
  1               5                  10                  15
Ser Gln Pro Leu Ser Leu Arg Pro Glu Ala Cys Arg Pro Ala Ala Gly
                 20                  25                  30
Gly Ala Val His Thr Arg Gly Leu Asp Phe Ala Cys Asp Ile Tyr Ile
             35                  40                  45
Trp Ala Pro Leu Ala Gly Thr Cys Gly Val Leu Leu Leu Ser Leu Val
         50                  55                  60
Ile Thr Leu Tyr Cys Lys Arg Gly Arg Lys Lys Leu Leu Tyr Ile Phe
 65                  70                  75                  80
Lys Gln Pro Phe Met Arg Pro Val Gln Thr Thr Gln Glu Glu Asp Gly
                 85                  90                  95
```

```
Cys Ser Cys Arg Phe Pro Glu Glu Glu Gly Gly Cys Glu Leu Arg
                100                 105                 110

Val Lys Phe Ser Arg Ser Ala Asp Ala Pro Ala Tyr Lys Gln Gly Gln
            115                 120                 125

Asn Gln Leu Tyr Asn Glu Leu Asn Leu Gly Arg Arg Glu Glu Tyr Asp
        130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
            210                 215                 220

<210> SEQ ID NO 21
<211> LENGTH: 244
<212> TYPE: PRT
<213> ORGANISM: Artificial sequence
<220> FEATURE:
<223> OTHER INFORMATION: synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Gly Gly Gly Gly Ser Gly
        115                 120                 125

Gly Gly Ser Gly Gly Gly Ser Asp Ile Gln Leu Thr Gln Ser
    130                 135                 140

Pro Ser Phe Leu Ser Ala Ser Val Gly Asp Arg Val Thr Ile Thr Cys
145                 150                 155                 160

Lys Ala Ser Gln Asn Val Asp Thr Asn Val Ala Trp Tyr Gln Gln Lys
                165                 170                 175

Pro Gly Lys Ala Pro Lys Ala Leu Ile Tyr Ser Ala Ser Tyr Arg Tyr
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220
```

-continued

```
Cys Gln Gln Tyr Asn Asn Tyr Pro Phe Thr Phe Gly Gln Gly Thr Lys
225                 230                 235                 240
Leu Glu Ile Lys
```

ANTI-CD276 CHIMERIC ANTIGEN RECEPTORS

CROSS-REFERENCE TO RELATED APPLICATION

This patent application is the U.S. national stage of International Patent Application Number PCT/US2016/050887, filed Sep. 9, 2016, which claims the benefit of U.S. Provisional Patent Application No. 62/216,447, filed Sep. 10, 2015, each of which is incorporated by reference in its entirety herein.

STATEMENT REGARDING FEDERALLY SPONSORED RESEARCH AND DEVELOPMENT

This invention was made with Government support under project number ZIABC011073 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 19,105 Byte ASCII (Text) file named "738172_ST25.txt," dated Mar. 6, 2018.

BACKGROUND OF THE INVENTION

Cancer is a public health concern. Despite advances in treatments such as chemotherapy, the prognosis for many cancers, including solid tumors, may be poor. Accordingly, there exists an unmet need for additional treatments for cancer, particularly solid tumors.

BRIEF SUMMARY OF THE INVENTION

An embodiment of the invention provides a chimeric antigen receptor (CAR) comprising: (a) an antigen binding domain comprising the amino acid sequences of each of SEQ ID NOs: 1-6, (b) a transmembrane domain, and (c) an intracellular T cell signaling domain.

Further embodiments of the invention provide related nucleic acids, recombinant expression vectors, host cells, populations of cells, conjugates, and pharmaceutical compositions relating to the polypeptides and proteins of the invention.

Additional embodiments of the invention provide methods of detecting the presence of cancer in a mammal and methods of treating or preventing cancer in a mammal.

BRIEF DESCRIPTION OF THE SEVERAL VIEWS OF THE DRAWINGS

FIG. 2A is a flow cytometric histogram of T cells activated with anti-CD3/anti-28 beads, then cultured with mock-vector supernatant (mock-transduced) or cultured with retroviral vector supernatant containing the CD276.MG.BB.z construct. Protein L is used to stain cell surface chimeric antigen receptors. The horizontal bar in the left panel indicates a value of 2.56. The horizontal bar in the right panel indicates a value of 54.7.

FIG. 2B is a flow cytometric dot plot of T cells activated with anti-CD3/anti-CD28 beads, then cultured with mock-vector supernatant (mock-transduced) or cultured with retroviral vector supernatant containing the CD276.MG.BB.z construct. Cells are stained with antibodies to Programmed Death Receptor 1 (PD-1) and LAG-3 as markers of T cell exhaustion. The values in the quadrants in the left panel are as follows: 0.0967 (top left quadrant), 0.0469 (top right quadrant), 83.7 (bottom left quadrant), and 16.1 (bottom right quadrant). The values in the quadrants in the right panel are as follows: 0.0761 (top left quadrant), 0.0415 (top right quadrant), 85.4 (bottom left quadrant), and 14.5 (bottom right quadrant).

FIG. 4A is a graph showing the amount of IFN-γ (pg/ml) secreted by effector T cells transduced with GFP (dotted bars) or a CD276.1CH2CH3.28z CAR (checkered bars), CD276.6.CH2CH3.28z CAR (horizontally striped bars), CD276.6.CH2CH3.BBz CAR (vertically striped bars), or CD276.17.CH2CH3.28.z CAR (diagonally striped bars) in response to co-culture with target cells: CHO cells transduced to express CD276 (CHO-276), Kelly (CD276⁺), RH18x (CD276⁺), 143B (CD276⁺), TC71 (CD276⁺), or AL (CD276⁺) cells. Tumor cells cultured alone (T alone) served as a control. The ratio of effector cells to target cells is shown in parentheses.

FIG. 4B is a graph showing the amount of IFN-γ (pg/ml) secreted by effector TI cells transduced with GFP (dotted bars) or a CD276.1.CH2CH3.28z (checkered bars), CD276.6.CH2CH3.28.z (horizontally striped bars), CD276.6.CH2CH3.BBz CAR (vertically striped bars), or CD276.17.CH2CH3.28.z (diagonally striped bars) in response to co-culture with target cells: CHO-K1 (CD276$^-$), CHO cells transduced to express CD276 (CHO-276), NALM6 (CD276$^-$), AL (CD276$^+$), AS (CD276$^+$), 143b (CD276$^+$), or K562 (CD276$^+$) cells. Tumor cells cultured alone (T alone) served as a control.

DETAILED DESCRIPTION OF THE INVENTION

Figure 1:
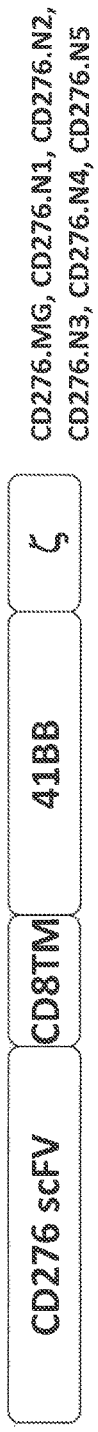
FIG. 1A is a schematic illustrating the structure of a "BBZ" anti-CD276 CAR, which includes an anti-CD276 scFv, a CD8 transmembrane (TM) domain, a 4-1 BB intracellular T cell signaling domain, and a CD3ζ intracellular T cell signaling domain (ζ). The anti-CD276 scFv comprised the antigen binding domain of the MGA271 (CD276.MG), CD276.N1, CD276.N2, CD276.N3, CD276.N4, or CD276.N5 antibody.
FIG. 1B is a schematic illustrating the structure of a "CH2CH3.BB.Z" anti-CD276 CAR, which includes an anti-CD276 scFv, an immunoglobulin CH2 and CH3 immunoglobulin G (IgG1) domain sequence (CH2CH3), a CD8 TM domain, a 4-1BB intracellular T cell signaling domain, and a CD3ζ intracellular T cell signaling domain (ζ). The anti-CD276 scFv comprised the antigen binding domain of the MGA271 (CD276.MG), CD276.N3, or CD276.6 antibody.
FIG. 1C is a schematic illustrating the structure of a "CH2CH3.28.Z" anti-CD276 CAR, which includes an anti-CD276 scFv, a CH2CH3 domain, a CD28 TM domain, a CD28 intracellular T cell signaling domain, and a CD3ζ intracellular T cell signaling domain (ζ). The anti-CD276 scFv comprised the antigen binding domain of the CD276.1, CD276.6, or CD276.17 antibody.
FIG. 1D is a schematic illustrating the structure of a "28.BB.Z" anti-CD276 CAR, which includes an anti-CD276 scFv, a CD28 TM domain, a CD28 intracellular T cell signaling domain, a 4-1 BB intracellular T cell signaling domain, and a CD3ζ intracellular T cell signaling domain (ζ). The anti-CD276 scFv comprised the antigen binding domain of the MGA271 (CD276.MG) antibody or the CD276.N3 antibody.
Figure 1:
Figure 1:
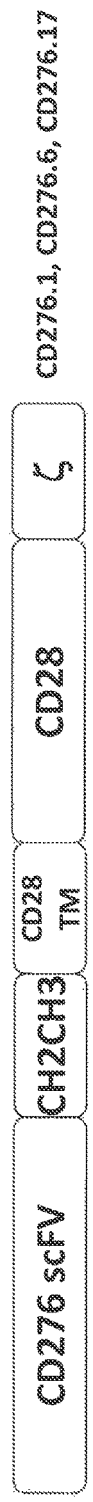
Figure 1:
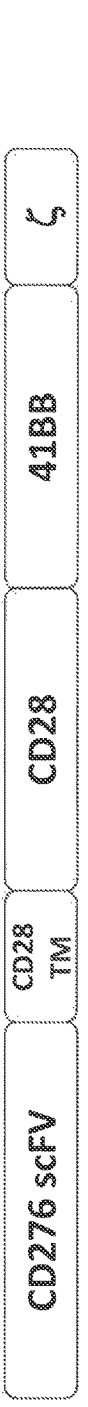

An embodiment of the invention provides a chimeric antigen receptor (CAR) comprising: (a) an antigen binding domain comprising the amino acid sequences of each of SEQ ID NOs: 1-6, (b) a transmembrane domain, and (c) an intracellular T cell signaling domain.

A CAR is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The CARs of the invention have antigen specificity for CD276 (also known as B7-H3). CD276 is expressed or overexpressed on a variety of human tumors, including pediatric solid tumors and adult carcinomas. Examples of cancers that express or overexpress CD276 include, but are not limited to, neuroblastoma, Ewing's sarcoma, rhabdomyosarcoma, and prostate, ovarian, colorectal, and lung cancers. Without being bound to a particular theory or mechanism, it is believed that by eliciting an antigen-specific response against CD276, the inventive CARs provide for one or more of the following: targeting and destroying CD276-expressing cancer cells, reducing or eliminating cancer cells, facilitating infiltration of immune cells to tumor site(s), and enhancing/extending anti-cancer responses.

The phrases "have antigen specificity" and "elicit antigen-specific response," as used herein, means that the CAR can specifically bind to and immunologically recognize antigen (CD276), such that binding of the CAR to the antigen elicits an immune response.

An embodiment of the invention provides a CAR comprising the antigen binding domain of the MGA271 antibody ("MGA271"). The antigen binding domain of MGA271 specifically binds to CD276. The MGA271 antibody is described in Loo et al., *Clin. Cancer Res.*, 18(14): 3834-45 (2012); WO 2011/109400; and U.S. Pat. No. 8,802,091, each of which is incorporated herein by reference.

The antigen binding domain may comprise any antigen binding portion of the MGA271 antibody. For example, the antigen binding domain may be a Fab fragment (Fab), F(ab')$_2$ fragment, diabody, triabody, tetrabody, single-chain variable region fragment (scFv), or a disulfide-stabilized variable region fragment (dsFv). In a preferred embodiment, the antigen binding domain is an scFv. An scFv is a truncated Fab fragment including the variable (V) domain of an antibody heavy chain linked to a V domain of an antibody light chain via a synthetic peptide, which can be generated using routine recombinant DNA technology techniques. The anti-CD276 antigen binding domain employed in the inventive CARs, however, are not limited to these exemplary types of antibody fragments.

The antigen binding domain may comprise a light chain variable region and/or a heavy chain variable region. In an embodiment of the invention, the heavy chain variable region comprises a complementarity determining region (CDR) 1 region, a CDR2 region, and a CDR3 region. In this regard, the antigen binding domain may comprise one or more of a heavy chain CDR1 region comprising the amino acid sequence of SEQ ID NO: 1; a heavy chain CDR2 region comprising the amino acid sequence of SEQ ID NO: 2; and a heavy chain CDR3 region comprising the amino acid sequence of SEQ ID NO: 3. Preferably, the heavy chain comprises all of the amino acid sequences of SEQ ID NOs: 1-3.

In an embodiment of the invention, the light chain variable region may comprise a light chain CDR1 region, a light chain CDR2 region, and a light chain CDR3 region. In this regard, the antigen binding domain may comprise one or more of a light chain CDR1 region comprising the amino acid sequence of SEQ ID NO: 4; a light chain CDR2 region comprising the amino acid sequence of SEQ ID NO: 5; and a light chain CDR3 region comprising the amino acid sequence of SEQ ID NO: 6. Preferably, the light chain comprises the amino acid sequences of all of SEQ ID NOs: 4-6. In an especially preferred embodiment, the antigen binding domain comprises all of the amino acid sequences of SEQ ID NO: 1-6.

The heavy chain variable region of the antigen binding domain may comprise, consist of, or consist essentially of the amino acid sequence of SEQ ID NO: 7. The light chain variable region of the antigen binding domain may comprise, consist of, or consist essentially of the amino acid sequence of SEQ ID NO: 8. Accordingly, in an embodiment of the invention, the antigen binding domain comprises a heavy chain variable region comprising the amino acid sequence of SEQ II) NO: 7 and/or a light chain variable region comprising the amino acid sequence of SEQ ID NO: 8. Preferably, the antigen binding domain comprises the amino acid sequences of both SEQ ID NOs: 7 and 8.

In an embodiment of the invention, the light chain variable region and the heavy chain variable region may be joined by a linker. The linker may comprise any suitable amino acid sequence. In an embodiment of the invention, the linker may comprise, consist, or consist essentially of, SEQ ID NO: 14. In an embodiment of the invention, the antigen binding domain comprises an scFv comprising the amino acid sequence of SEQ ID NO: 21.

In an embodiment of the invention, the antigen binding domain comprises a leader sequence. The leader sequence may be positioned at the amino terminus of the light chain variable region or the heavy chain variable region. Preferably, the leader sequence is positioned at the amino terminus of the heavy chain variable region. The leader sequence may comprise any suitable leader sequence. For example, the antigen binding domain may comprise a leader sequence comprising, consisting of, or consisting essentially of SEQ ID NO: 13. In an embodiment of the invention, while the leader sequence may facilitate expression of the CAR on the surface of the cell, the presence of the leader sequence in an expressed CAR may not be necessary in order for the CAR to function. In an embodiment of the invention, upon expression of the CAR on the cell surface, the leader sequence may be cleaved off of the CAR. Accordingly, in an embodiment of the invention, the CAR lacks a leader sequence.

In an embodiment of the invention, the CAR may comprise an immunoglobulin constant domain. Preferably, the immunoglobulin domain is a human immunoglobulin sequence. In an embodiment, the immunoglobulin constant domain comprises an immunoglobulin CH2 and CH3 immunoglobulin G (IgG1) domain sequence (CH2CH3). Without being bound to a particular theory or mechanism, it is believed that the CH2CH3 domain may extend the binding motif of the scFv away from the membrane of the CAR-expressing cells and may more accurately mimic the size and domain structure of a native TCR. In some embodiments, the CAR may lack an immunoglobulin constant domain.

In an embodiment of the invention, the CAR comprises a transmembrane (TM) domain. The TM domain may comprise the TM domain of one or both of CD8 and CD28. In a preferred embodiment, the CD8 and CD28 are human. In this regard, the TM domain may comprise any one or more of the CD8 TM domain amino acid sequence of SEQ ID NO:

9, the CD28 TM domain amino acid sequence of SEQ ID NO: 15, and the CD8 TM domain amino acid sequence of SEQ ID NO: 16. Preferably, the TM domain comprises the CD8 TM domain amino acid sequence of SEQ ID NO: 9.

In an embodiment of the invention, the CAR comprises an intracellular T cell signaling domain. The intracellular T cell signaling domain may comprise an intracellular T cell signaling domain of any one or more of CD28, 4-1 BB, and CD3 zeta (ζ). In a preferred embodiment, the CD28, CD137, and CD3ζ are human. CD28 is a T cell marker important in T cell co-stimulation. CD137, also referred to as 4-1 BB, transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). In this regard, the intracellular T cell signaling domain may comprise any one or more of the CD28 intracellular T cell signaling domain amino acid sequence of SEQ ID NO: 17, the 4-1BB intracellular T cell signaling domain amino acid sequence of SEQ ID NO: 18, the 4-1 BB intracellular T cell signaling domain amino acid sequence of SEQ ID NO: 10, and the CD3ζ intracellular T cell signaling domain amino acid sequence of SEQ ID NO: 11. Preferably, the intracellular T cell signaling domain comprises the 4-1BB intracellular T cell signaling domain amino acid sequence of SEQ ID NO: 10 and the CD3 intracellular T cell signaling domain amino acid sequence of SEQ ID NO: 11.

In an embodiment of the invention, the CAR comprises the transmembrane domain of CD8, the intracellular T cell signaling domain of 4-1 BB, and the intracellular T cell signaling domain of CD3 zeta. In this regard, the CAR may comprise (i) the amino acid sequences of all of SEQ ID NOs: 9-11 or (ii) the amino acid sequence of SEQ II) NO: 20. Preferably, the CAR comprises (a) the amino acid sequences of all of SEQ ID NOs: 1-6 and 9-11; (b) the amino acid sequences of all of SEQ ID NOs: 7-11; (c) the amino acid sequences of all of SEQ ID NOs: 1-6 and 20; (d) the amino acid sequences of all of SEQ ID NOs: 7-8 and 20.

An embodiment of the invention provides a CAR comprising the amino acid sequence of SEQ ID NO: 12. The components of the CAR comprising the amino acid sequence of SEQ ID NO: 12 are set forth in Table 1.

TABLE 1

| SEQ ID NO: | Antigen Binding Domain | Further Components |
|---|---|---|
| SEQ ID NO: 12 | MGA271 scFv (SEQ ID NO: 21) | CD8 TM domain (SEQ ID NO: 9) 4-1BB and CD3ζ intracellular T cell signaling domains (SEQ ID NOs: 10-11) |

Included in the scope of the invention are functional variants of the inventive CARs described herein. The term "functional variant" as used herein refers to a CAR having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., lie, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the CAR or functional variant.

The CARs of embodiments of the invention can be of any length, i.e., can comprise any number of amino acids, provided that the polypeptides, proteins, or CARs retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention can be glycosylated, amidated, carboxylated, phosphorylated, esterified, N-acylated, cyclized via, e.g., a disulfide bridge, or converted into an acid addition salt and/or optionally dimerized or polymerized.

The CARs of embodiments of the invention can be obtained by methods known in the art. The CARs may be made by any suitable method of making polypeptides or proteins. Suitable methods of de novo synthesizing polypeptides and proteins are known in the art. Also, the CARs can be recombinantly produced using the nucleic acids described herein using standard recombinant methods as described in, for example, Green and Sambrook, *Molecular Cloning: A Laboratory Manual* (4th Ed.), Cold Spring Harbor Laboratory Press (2012). Alternatively, the CARs described herein can be commercially synthesized by companies, such as Synpep (Dublin, Calif.) and Multiple Peptide Systems (San Diego, Calif.). In this respect, the inventive CARs can be synthetic and/or recombinant.

Further provided by an embodiment of the invention is a nucleic acid comprising a nucleotide sequence encoding any of the CARs described herein. The nucleic acids of the invention may comprise a nucleotide sequence encoding any one or more of the leader sequences, linkers, antigen binding domains, immunoglobulin domains, transmembrane domains, and intracellular T cell signaling domains described herein. For example, the nucleic acids may comprise a nucleotide sequence encoding a CAR comprising the amino acid sequence of SEQ ID NO: 12, the nucleic acid comprising the nucleotide sequence of SEQ ID NO: 19.

"Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the polypeptide, protein, or CAR and which may or may not be translated upon expression of the nucleic acid by a host cell (e.g., AAA).

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded CAR, polypeptide, protein, or functional variant.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs described herein. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs described herein. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to the nucleotide sequence of any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, Calif.), the pET series (Novagen, Madison, Wis.), the pGEX series (Pharmacia Biotech, Uppsala, Sweden), and the pEX series (Clontech. Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

In an embodiment, the recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColEl, 2λ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive CARs, or to the nucleotide sequence which is complementary to or which hybridizes to the nucleotide sequence encoding the inventive CARs. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell or a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naïve T cells, and the like. The T cell may be a CD8$^+$ T cell or a CD4$^+$ T cell.

Also provided by an embodiment of the invention is a population of cells comprising at least two of the host cells described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the number of cells in the population may be rapidly expanded. Expansion of the numbers of cells expressing the CAR can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of cells is carried out by culturing the T cells with OKT3 antibody, IL-2, and feeder PBMC (e.g., irradiated allogeneic PBMC).

The CARs, nucleic acids, recombinant expression vectors, and host cells (including populations thereof), all of which are collectively referred to as "inventive anti-CD276 materials" hereinafter, can be isolated and/or purified. The term "isolated," as used herein, means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-CD276 materials can be formulated into a composition, such as a pharmaceutical composition. In this regard, an embodiment of the invention provides a pharmaceutical composition comprising any of the inventive anti-CD276 materials described herein and a pharmaceutically acceptable carrier. The inventive pharmaceutical compositions containing any of the inventive anti-CD276 materials can comprise more than one inventive anti-CD276 material, e.g., a CAR and a nucleic acid. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

Preferably, the carrier is a pharmaceutically acceptable carrier. With respect to pharmaceutical compositions, the carrier can be any of those conventionally used for the particular inventive CAR material under consideration. Methods for preparing administrable compositions are known or apparent to those skilled in the art and are described in more detail in, for example, *Remington: The Science and Practice of Pharmacy*, 22$^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, interperitoneal, or intrapleural administration. More than one route can be used to administer the inventive CAR materials, and in certain instances, a particular route can provide a more immediate and more effective response than another route.

Preferably, the inventive CAR material is administered by injection, e.g., intravenously. When the inventive CAR material is a host cell (or a population thereof) expressing the inventive CAR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier may be supplemented with human serum albumen.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the anti-CD276 material selected, method of administration, timing and frequency of administration, the existence, nature, and extent of any adverse side-effects that might accompany the administration of a particular anti-CD276 material, and the desired physiological effect. It will be appreciated by one of skill in the art that various diseases or disorders (e.g., cancer) could require prolonged treatment involving multiple administrations, perhaps using the inventive anti-CD276 material(s) in each or various rounds of administration.

The dose of the inventive CAR material also will be determined by the existence, nature and extent of any adverse side effects that might accompany the administration of a particular inventive CAR material. Typically, the attending physician will decide the dosage of the inventive CAR material with which to treat each individual patient, taking into consideration a variety of factors, such as age, body weight, general health, diet, sex, inventive CAR material to be administered, route of administration, and the severity of the cancer being treated. In an embodiment in which the inventive CAR material is a population of cells, the number of cells administered per infusion may vary, e.g., from about $1\times10^6$ to about $1\times10^{12}$ cells or more.

For purposes of the invention, the amount or dose of the inventive anti-CD276 material administered should be sufficient to effect a therapeutic or prophylactic response in the subject or mammal over a reasonable time frame. For example, the dose of the inventive anti-CD276 material should be sufficient to bind to CD276, or detect, treat or prevent cancer in a period of from about 2 hours or longer, e.g., about 12 to about 24 or more hours, from the time of administration. In certain embodiments, the time period could be even longer. The dose will be determined by the efficacy of the particular inventive anti-CD276 material and the condition of the mammal (e.g., human), as well as the body weight of the mammal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which each is given a different dose of the T cells, could be used to determine a starting dose to be administered to a mammal. The extent to which target cells are lysed and/or IFN-γ is secreted upon administration of a certain dose can be assayed by methods known in the art.

One of ordinary skill in the art will readily appreciate that the inventive anti-CD276 materials of the invention can be modified in any number of ways, such that the therapeutic or prophylactic efficacy of the inventive anti-CD276 materials is increased through the modification. For instance, the inventive anti-CD276 materials can be conjugated either directly or indirectly through a bridge to a chemotherapeutic agent. The practice of conjugating compounds to a chemotherapeutic agent is known in the art. One of ordinary skill in the art recognizes that sites on the inventive anti-CD276 materials, which are not necessary for the function of the inventive TCR materials, are ideal sites for attaching a bridge and/or a chemotherapeutic agent, provided that the bridge and/or chemotherapeutic agent, once attached to the inventive anti-CD276 materials, do(es) not interfere with the function of the inventive anti-CD276 materials, i.e., the ability to bind to CD276 or to detect, treat, or prevent cancer.

When the inventive anti-CD276 material(s) are administered with one or more additional therapeutic agents, one or more additional therapeutic agents can be coadministered to the mammal. By "coadministering" is meant administering one or more additional therapeutic agents and the inventive CAR material(s) sufficiently close in time such that the inventive anti-CD276 material(s) can enhance the effect of one or more additional therapeutic agents, or vice versa. In this regard, the inventive anti-CD276 material(s) can be administered first and the one or more additional therapeutic agents can be administered second, or vice versa. Alternatively, the inventive anti-CD276 material(s) and the one or more additional therapeutic agents can be administered simultaneously. An exemplary therapeutic agent that can be co-administered with the anti-CD276 material(s) is IL-2. Without being bound to a particular theory or mechanism, it is believed that IL-2 may enhance the therapeutic effect of the inventive anti-CD276 material(s). For purposes of the inventive methods, wherein host cells or populations of cells are administered to the mammal, the cells can be cells that are allogeneic or autologous to the mammal.

It is contemplated that the inventive anti-CD276 materials and pharmaceutical compositions can be used in methods of treating or preventing cancer in a mammal. Without being bound to a particular theory or mechanism, the inventive anti-CD276 CARs have biological activity, e.g., ability to recognize CD276, such that the anti-CD276 CAR, when expressed by a cell, is able to mediate an immune response against the cell expressing the CD276, for which the anti-CD276 CAR is specific. In this regard, an embodiment of the invention provides a method of treating or preventing cancer in a mammal, comprising administering to the mammal any of the CARs, nucleic acids, recombinant expression vectors, host cells, population of cells, and/or pharmaceutical compositions of the invention in an amount effective to treat or prevent cancer in the mammal.

An embodiment of the invention further comprises lymphodepleting the mammal prior to administering the inventive anti-CD276 material(s). Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, rhabdomyosarcoma, bladder cancer (e.g., bladder carcinoma), bone cancer (e.g., osteosarcoma), brain cancer (e.g., medulloblastoma, glioblastoma, or glioma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, erythroleukemia, Ewing's sarcoma, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a solid tumor (e.g., a pediatric solid tumor), carcinoma (e.g., adult carcinoma), neuroblastoma, Ewing's sarcoma, rhabdomyosarcoma, Wilm's tumor, prostate cancer, ovarian cancer, colorectal cancer, or lung cancer. Preferably, the cancer is characterized by the expression or overexpression of CD276.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, e.g., cancer, or a symptom or condition thereof. Alternatively or additionally, "prevention" can encompass delaying the recurrence of the disease, e.g., cancer, or a symptom or condition thereof.

Another embodiment of the invention provides any of the CARs, nucleic acids, recombinant expression vectors, host cells, population of cells, or pharmaceutical compositions of the invention for use in the treatment or prevention of cancer in a mammal. The cancer may any of the cancers described herein with respect to other aspects of the invention.

Another embodiment of the invention provides a method of detecting the presence of cancer in a mammal, comprising: (a) contacting a sample comprising one or more cells from the mammal with any of the CARs, nucleic acids, recombinant expression vectors, host cells, population of cells, or pharmaceutical compositions of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including tumor cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, nucleic acids, recombinant expression vectors, host cells, populations of cells, or pharmaceutical compositions described herein can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing an anti-CD276 material for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, anti-CD276 material function can be evaluated by measurement of cellular cytotoxicity, as described in Zhao et al., *J. Immunol.*, 174: 4415-4423 (2005).

The following examples further illustrate the invention but, of course, should not be construed as in any way limiting its scope.

Example 1

This example demonstrates that cells transduced with a retrovirus encoding the CD276.MG.BB.z CAR (SEQ ID NO: 12) are efficiently transduced and express the CAR.

Human T cells were activated with anti-CD3/CD28 beads, then transduced with a retroviral vector encoding the CD276.MG.BB.z CAR (SEQ ID NO: 12) (FIG. 1A). Efficient transduction and CAR expression was demonstrated by binding to protein L (FIG. 2A). Protein L is a bacterial protein that specifically binds to the light chain of immunoglobulin. Therefore, the binding of a cell to protein L identifies cells expressing a scFv, which includes a light chain variable fragment.

Example 2

This example demonstrates that cells transduced with a retroviral vector encoding the CD276.MG.BB.z CAR (SEQ ID NO: 12) show no evidence of early exhaustion as assessed by LAG3 and PD-1 expression.

Human T cells were transduced with a retroviral vector encoding the CD276.MG.BB.z CAR (SEQ ID NO: 12) as described in Example 1. LAG3 and PD-1 expression on the transduced cells was measured by flow cytometry. An absence of LAG3 expression and an absence of high level PD-1 expression was observed, indicating that the transduced T cells showed no evidence of early exhaustion as measured by LAG3 and PD-1 expression (FIG. 2B).

Example 3

This example demonstrates the robust expansion of the numbers of cells transduced with a retroviral vector encoding the CD276.MG.BB.z CAR (SEQ ID NO: 12) when maintained in culture following transduction.

Figure 3:
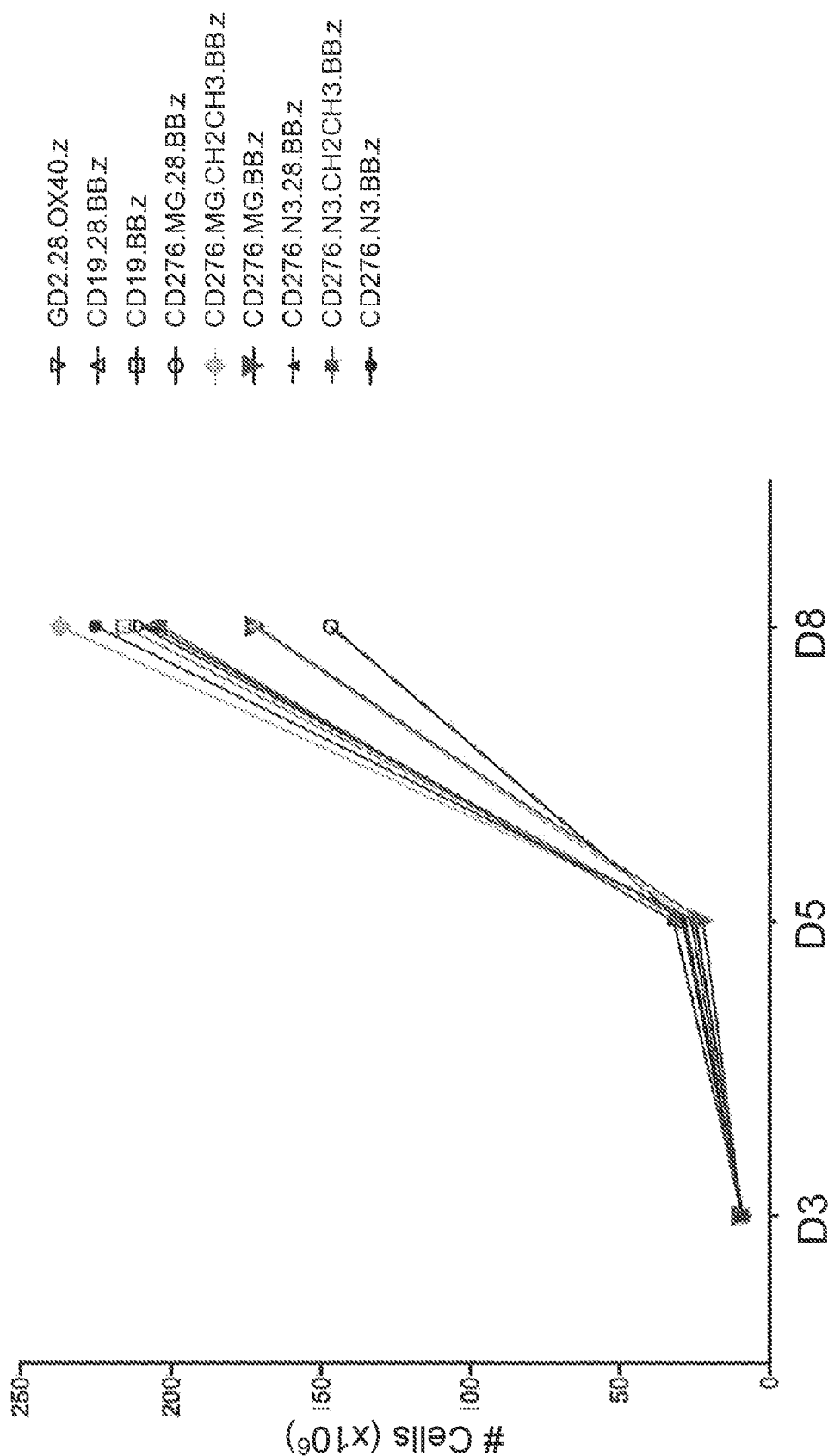
FIG. 3 is a graph showing the number ($\times 10^6$) of transduced cells at various time points (days) in culture. The cells were transduced with one of the following CARs: GD2 OX40Z (▽), CD19 28BBZ (Δ), CD19 BB3Z (□), CD276.MG 28BBZ (○) (FIG. 1D), CD276.MG CH2CH3BBZ (♦) (FIG. 1B), CD276.MG BBZ (▼) (FIG. 1A) (SEQ ID NO: 12), CD276.N3 28BBZ (▲) (FIG. 1D), CD276.N3 CH2CH3BBZ (■) (FIG. 1B), or CD276.N3 BBZ (●) (FIG. 1A).

Human T cells were transduced as described in Example 1 with a retroviral vector encoding one of the CARs shown in FIG. 3, one of which was the CD276.MG.BB.z CAR (SEQ ID NO: 12). The GD2 OX40Z CAR contained the antigen binding domain of an anti-GD2 antibody, the OX40 intracellular T cell signaling domain, and the CD3f intracellular T cell signaling domain. The CD19 28BBZ CAR had the structure shown in FIG. 1D with the exception that the anti-CD276 antigen binding domain was replaced with an anti-CD19 antigen binding domain. The CD19 BBZ CAR had the structure shown in FIG. 1A with the exception that the anti-CD276 antigen binding domain was replaced with an anti-CD19 antigen binding domain.

The transduced cells were maintained in culture for up to eight days. The numbers of cells were counted on Day 8. The results are shown in FIG. 3. As shown in FIG. 3, the number of cells transduced with the CD276.MG.BB.z CAR (SEQ ID NO: 12) increased from less than about 25×10$^6$ on Day 3 to over 150×10$^6$ on Day 8 of the culture. These results showed the robust expansion of the numbers of cells transduced with a retroviral vector encoding the CD276.MG.BB.z CAR (SEQ ID NO: 12) when maintained in culture following transduction without evidence of fratricide or apoptosis associated with early exhaustion.

Example 4

This example demonstrates that cells expressing the CD276.MG.BB.z CAR (SEQ ID NO: 12) secrete higher levels of IFN-γ in response to co-culture with CD276-expressing target cells as compared to cells expressing a CAR comprising the antigen binding domain of the CD276.1, a CD276.6, or CD276.17 antibody.

Human T cells were transduced with green fluorescent protein (GFP), a CD276.1.CH2CH3.28.z CAR, a CD276.6.CH2CH3.28.z CAR, a CD276.6.CH2CH3.BB.z CAR, or a CD276.17.CH2CH3.28.z CAR. The transduced CARs (effector cells) were co-cultured alone or with CD276-expressing target cells at the effector cell:target cell ratios shown in FIG. 4A. IFN-γ was measured. The results are shown in FIG. 4A. As shown in FIG. 4A, the cells expressing the CD276.1 CAR secreted higher amounts of IFN-γ in response to co-culture with CD276-expressing target cells as compared to the CD276.6.CH2CH3.28.z CAR, the CD276.6.CH2CH3.BB.z CAR, or the CD276.17.CH2CH3.28.z CAR.

In a second experiment, the transduced cells were co-cultured with the CD276-expressing target cells shown in FIG. 4B. CHO-K1 and NALM6 are CD276-negative cell lines that served as negative controls. IFN-γ was measured. The results are shown in FIG. 4B. As shown in FIG. 4B, the cells expressing the CD276.1 CAR secreted higher amounts of IFN-γ in response to co-culture with CD276-expressing target cells as compared to the CD276.6.CH2CH3.28.z CAR, the CD276.6.CH2CH3.BB.z CAR, or the CD276.17.CH2CH3.28.z CAR.

Figure 4C:
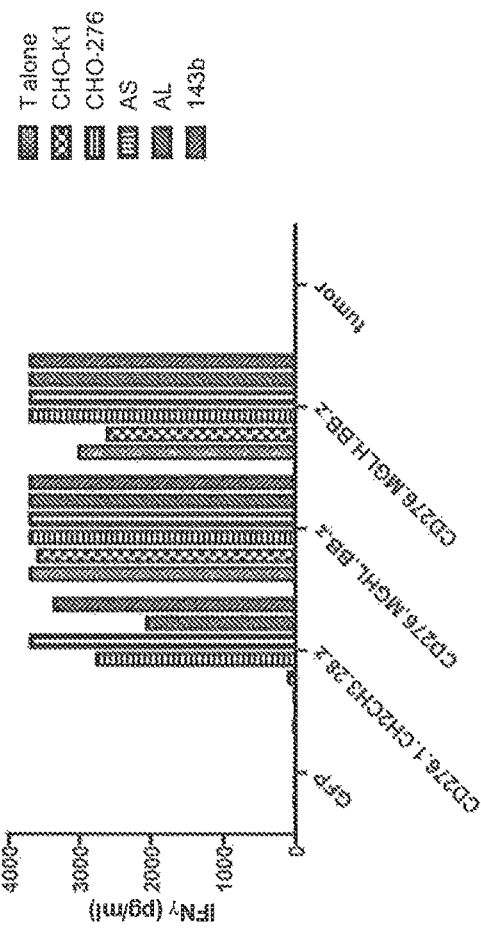
FIG. 4C is a graph showing the amount of IFN-γ (pg/ml) secreted by effector T cells transduced with GFP, a CD276.1.CH2CH3.28.z CAR, the CD276.MG.BB.z CAR (with the heavy chain positioned adjacent to the amino terminus of the linker and the light chain positioned adjacent to the carboxyl terminus of the linker) (SEQ ID NO: 12) (CD276.MGHL), or the CD276.MG.BB.z CAR (with the heavy chain positioned adjacent to the carboxyl terminus of the linker and the light chain positioned adjacent to the amino terminus of the linker) (CD276.MGLH) in response to co-culture with target cells CHO-K1 (CD276$^-$) (checkered bars), CHO cells transduced to express CD276 (CHO-276) (horizontally striped bars), AS tumor cells (CD276$^+$) (vertically striped bars), AL tumor cells (CD276$^+$) (//), or 143b tumor cells (CD276$^+$) (††). Tumor cells cultured alone (T alone) (dotted bars) served as a control.

The CD276.1 CAR was determined to provide the best function among those tested in FIGS. 4A and 4B. The function of the CD276.1 CAR was then compared to that of CD276.MG.BB.z CAR (SEQ ID NO: 12). Human T cells were transduced with GFP, the CD276.1 CAR, the CD276.MG.BB.z CAR (with the heavy chain positioned adjacent to the amino terminus of the linker and the light chain positioned adjacent to the carboxyl terminus of the linker) (SEQ ID NO: 12) (CD276.MGHL), or the CD276.MG.BB.z CAR (with the heavy chain positioned adjacent to the carboxyl terminus of the linker and the light chain positioned adjacent to the amino terminus of the linker) (CD276.MGLH). The transduced cells were co-cultured with the CD276-expressing target cells CHO-276, AS (neuroblastoma), AL (rhabdomyosarcoma), or 143b (osteosarcoma). As controls, tumor cells were cultured alone or with the CD276$^-$ cell CHO-K1. IFN-γ was measured. The results are shown in FIG. 4C. As shown in FIG. 4C, the cells expressing the CD276.MG.BB.z CAR secreted higher amounts of IFN-γ in response to co-culture with CD276-expressing target cells as compared to the 276.1 CAR. No difference in potency was observed based on the arrangement of the heavy and light chains in the CD276.MG.BB.z CAR.

Figure 4D:
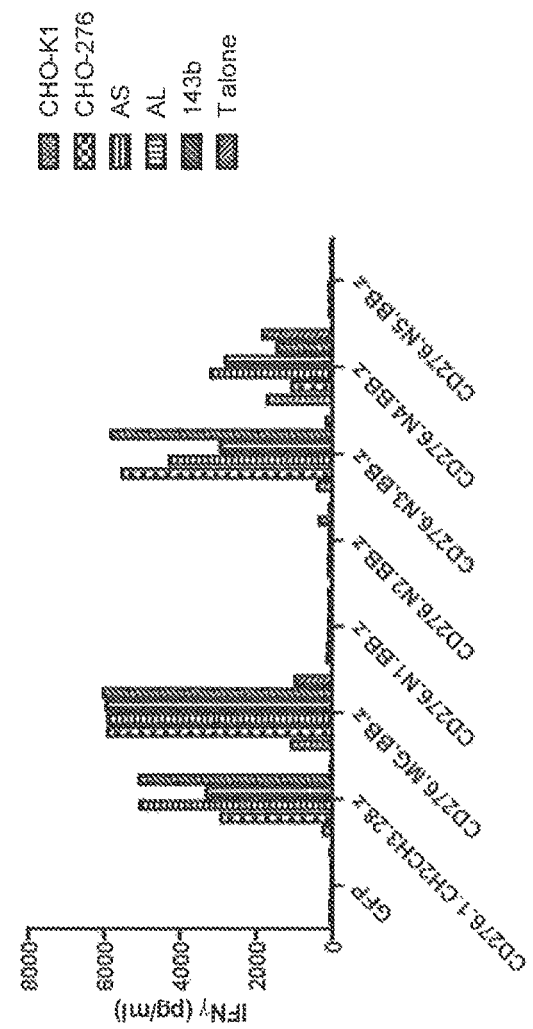
FIG. 4D is a graph showing the amount of IFN-γ (pg/ml) secreted by effector T cells transduced with GFP, the CD276.MG.BB.z CAR (SEQ ID NO: 12) (CD276.MG), a CD276.1.CH2CH3.28.z CAR, CD276.N1.BB.z CAR, CD276.N2.BB.z CAR, CD276.N3.BB.z CAR, CD276.N4.BB.z CAR, or CD276.N5.BB.z CAR in response to co-culture with target cells: CHO-K1 (CD276$^+$) (dotted bars), CHO cells transduced to express CD276 (CHO-276) (checkered bars), AS tumor cells (CD276) (horizontally striped bars), AL tumor cells (CD276$^+$) (vertically striped bars), or 143b tumor cells (CD276) (//). Tumor cells cultured alone (T alone) (††) served as a control.

In a separate experiment, human T cells were transduced with GFP, the CD276.1.CH2CH3.28.z CAR, the CD276.MG.BB.z CAR (SEQ ID NO: 12), the CD276.N1.BB.z CAR, the CD276.N2.BB.z CAR, the CD276.N3.BB.z CAR, the CD276.N4.BB.z CAR, or the CD276.N5.BB.z CAR. The transduced cells were co-cultured with the CD276-expressing target cells CHO-276, AS, AL, or 143b. As controls, tumor cells were cultured alone or with the CD276$^-$ cell CHO-K1. IFN-γ was measured. The results are shown in FIG. 4D. As shown in FIG. 4D, cells expressing the CD276.MG.BB.z CAR (SEQ ID NO: 12) secreted higher levels of IFN-γ in response to co-culture with CD276-expressing target cells as compared to cells expressing the other CARs tested.

Example 5

This example demonstrates that cells expressing the CD276.MG.BB.z CAR (SEQ ID NO: 12) secrete higher levels of IFN-γ in response to co-culture with CD276-expressing target cells as compared to cells expressing a CAR comprising the antigen binding domain of the anti-CD276 N1, N2, N4 or N5 antibody.

Figure 5:
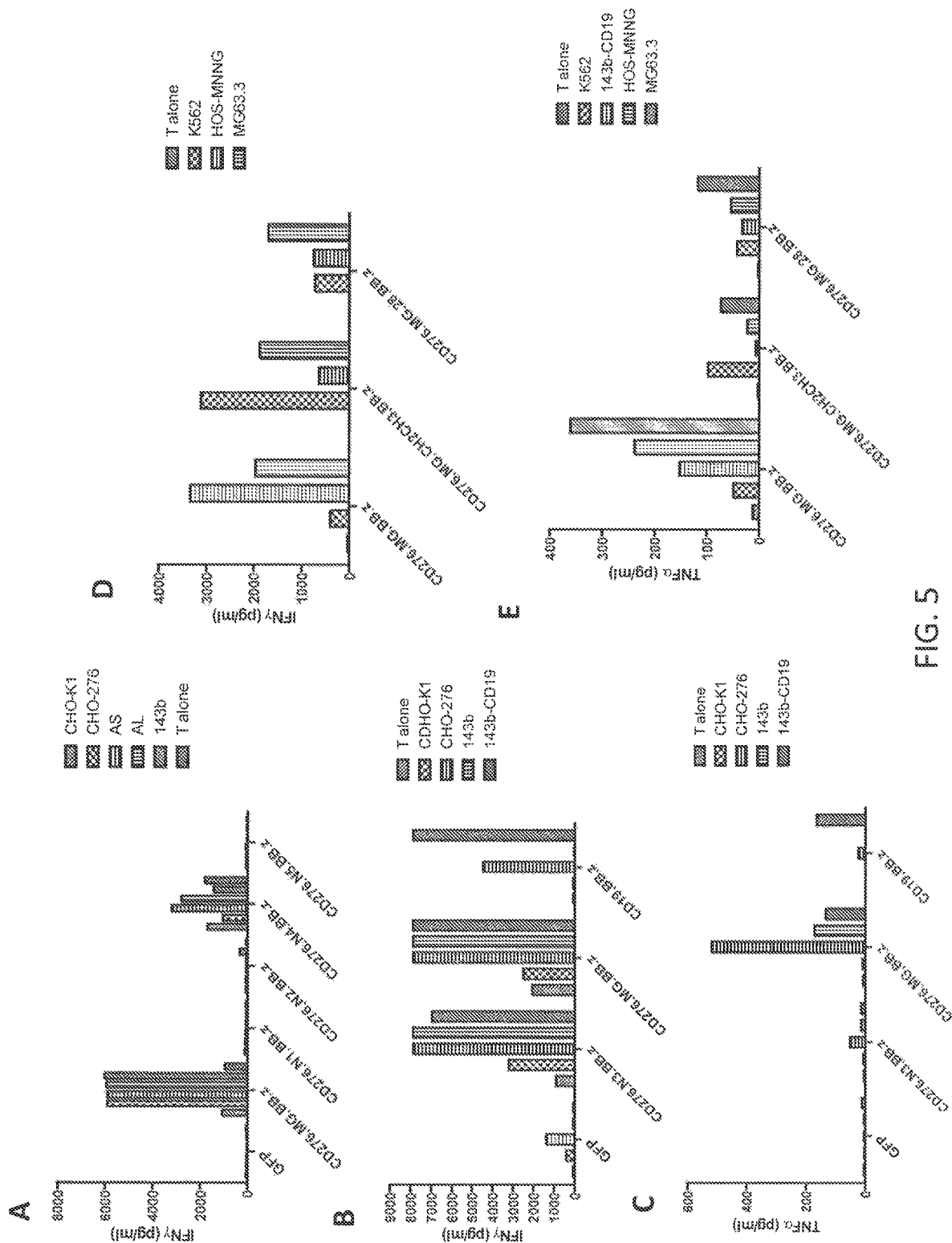
FIG. 5A is a graph showing the amount of IFN-γ (pg/ml) secreted by effector T cells transduced with GFP, the CD276.MG.BB.z CAR (SEQ ID NO: 12) (CD276.MG), or a CD276.N1.BB.z CAR, CD276.N2.BB.z CAR, CD276.N4.BB.z CAR, or CD276.N5.BB.z CAR in response to co-culture with target cells CHO-K1 (CD276$^-$) (dotted cells), CHO cells transduced to express CD276 (CHO-276) (checkered bars), AS tumor cells (CD276$^+$) (horizontally striped bars), AL tumor cells (CD276$^+$) (vertically striped bars), or 143b tumor cells (CD276$^+$) (//). Tumor cells cultured alone (T alone) (††) served as a control.
FIG. 5B is a graph showing the amount of IFN-γ (pg/ml) secreted by effector T cells transduced with GFP, the CD276.MG.BB.z CAR (SEQ ID NO: 12) (CD276.MG), a CD276.N3.BB.z CAR, or a CD19.BB.z CAR in response to co-culture with target cells CHO-K1 (CD276$^-$) (checkered bars), CHO-276 (CD276$^+$) (horizontally striped bars), 143b tumor cells (CD276$^+$) (vertically striped bars), or 143b cells transduced to express CD19 (143b-CD19) (//). Tumor cells cultured alone (T alone) (dotted bars) served as a control.
FIG. 5C is a graph showing the amount of TNF-α (pg/ml) secreted by effector T cells transduced with GFP, the CD276.MG.BB.z CAR (SEQ II) NO: 12) (CD276.MG), CD276.N3.BB.z CAR, or a CD19.BB.z CAR in response to co-culture with target cells CHO-K1 (CD276$^-$) (checkered bars), CHO-276 (CD276$^+$) (horizontally striped bars), 143b tumor cells (CD276$^+$) (vertically striped bars), or 143b cells transduced to express CD19 (143b-CD119) (//). Tumor cells cultured alone (T alone) (dotted bars) served as a control.
FIG. 5D is a graph showing the amount of IFN-γ (pg/ml) secreted by effector T cells transduced with the CD276.MG.BB.z CAR (SEQ ID NO: 12) (MG-BBZ) (FIG. 1A), the CD276.MG.CH2CH3.BB.z CAR (FIG. 1B) (MG-CH2CH3-BBZ), or the CD276.MG.28BB.z CAR (FIG. 1D) (MG-28-BBZ) in response to co-culture with target cells K562 (CD276$^{+)}$ (checkered bars), HOS-MNNG (CD276$^+$) (horizontally striped bars), or MG63.3 (CD276$^+$) (vertically striped bars). Tumor cells cultured alone (T alone) (dotted bars) served as a control.
FIG. 5E is a graph showing the amount of TNF-α (pg/ml) secreted by effector T cells transduced with the CD276.MG.BB.z CAR (SEQ ID NO: 12) (MG-BBZ) (FIG. 1A), the CD276.MG.CH2CH3.BB.z CAR (FIG. 1B) (MG-CH2CH3-BBZ), or the CD276.MG.28BB.z CAR (FIG. 1D) (MG-28-BBZ) in response to co-culture with target cells K562 (checkered bars), HOS-MNNG (vertically striped bars), MG63.3 (//), or 143b cells (horizontally striped bars) transduced to express CD19 (143b-CD19). Tumor cells cultured alone (T alone) (dotted bars) served as a control.

Human T cells were transduced with GFP, CD276.MG.BB.z CAR (SEQ ID NO: 12), a CD276.N1.BB.z CAR, CD276.N2.BB.z CAR, CD276.N4.BB.z CAR, or a CD276.N5.BB.z CAR. The transduced cells (effector cells) were co-cultured with the CD276-expressing target cells CHO-276, AS, AL, or 143b. Tumor cells cultured alone and transduced cells cultured with CD276$^-$ CHO-K cells served as controls. IFN-γ was measured. The results are shown in FIG. 5A. As shown in FIG. 5A, the cells expressing the CD276.MG.BB.z CAR (SEQ ID NO: 12) secreted higher amounts of IFN-γ in response to co-culture with CD276-expressing target cells as compared to a CAR comprising the antigen binding domain of the N1, N2, N4 or N5 antibody.

Example 6

This example demonstrates that cells expressing the CD276.MG.BB.z CAR (SEQ ID NO: 12) secrete similar levels of IFN-γ, but higher levels of TNF-α, in response to co-culture with CD276-expressing target cells as compared to cells expressing a CAR comprising the antigen binding domain of the anti-CD276 N3 antibody.

Human T cells were transduced with GFP, CD276.MG.BB.z CAR (SEQ ID NO: 12) (CD276.MG), a CD276.N3.BB.z CAR, or an anti-CD19.BB.z CAR. The transduced cells (effector cells) were co-cultured with the CD276-expressing target cells CHO-276 or 143b or 143b cells transduced to express CD19 (143b-CD19). Tumor cells cultured alone and transduced cells cultured with CD276$^-$ CHO-K1 cells served as controls. IFN-γ was measured. The results are shown in FIG. 5B. As shown in FIG. 5B, the cells expressing the CD276.MG.BB.z CAR (SEQ ID NO: 12) secreted similar amounts of IFN-γ in response to co-culture with CD276-expressing target cells as compared to a CAR comprising the antigen binding domain of the CD276.N3 antibody.

In a separate experiment, the transduced cells (effector cells) were co-cultured with the CD276-expressing target cells CHO-276 cells, 143b cells, or 143b-CD19 cells. Tumor cells cultured alone and transduced cells cultured with CD276$^-$ CHO-K1 cells served as controls. TNF-α was measured. The results are shown in FIG. 5C. As shown in FIG. 5C, the cells expressing the CD276.MG.BB.z CAR (SEQ ID NO: 12) secreted higher amounts of TNF-α in response to co-culture with CD276-expressing target cells as compared to a CAR comprising the antigen binding domain of the CD276.N3 antibody.

Example 7

This example demonstrates that cells expressing the CD276.MG.BB.z CAR (SEQ ID NO: 12) (FIG. 1A), which lacks a CH2CH3 domain, secrete similar levels of IFN-γ, but higher levels of TNF-α, in response to co-culture with CD276-expressing target cells as compared to cells expressing the CD276.MG.CH2CH3.BB.z CAR (FIG. 1B) or the CD276.MG.28.BB.z CAR (FIG. 1D).

Human T cells were transduced with three different versions of CARs comprising the antigen binding domain of the MGA271 antibody: the CD276.MG.BB.z CAR (SEQ ID NO: 12) (FIG. 1A) (which lacks a CH2CH3 domain), the CD276.MG.CH2CH3.BB.z CAR (FIG. 1B) (which has a CH2CH3 domain) or the CD276.MG.28.BB.z CAR (FIG. 1D) (which has a CD28 intracellular signaling domain in addition to the 4-1BB and CD3 signaling domains).

The transduced cells (effector cells) were co-cultured with the CD276-expressing target cells K562 (human erythroleukemia cell line), HOS-MNNG (human osteosarcoma cell line), or MG63.3 (human osteosarcoma cell line). Tumor cells cultured alone served as controls. IFN-γ was measured. The results are shown in FIG. 5D. As shown in FIG. 5D, the cells expressing the CD276.MG.BB.z CAR (SEQ ID NO: 12) secreted similar amounts of IFN-γ in response to co-culture with CD276-expressing target cells as compared to cells expressing the CD276.MG.CH2CH3.BB.z CAR or the CD276.MG.28BB.z CAR.

In a separate experiment, the transduced cells (effector cells) were co-cultured with the CD276-expressing target cells K562, HOS-MNNG, or MG63.3. Tumor cells cultured alone served as controls. TNF-α was measured. The results are shown in FIG. 5E. As shown in FIG. 5E, the cells expressing the CD276.MG.BB.z CAR (SEQ ID NO: 12) secreted higher amounts of TNF-α in response to co-culture with CD276-expressing target cells as compared to cells expressing the CD276.MG.CH2CH3.BB.z CAR or the CD276.MG.28.BB.z CAR.

Example 8

This example demonstrates that cells expressing the CD276.MG.BB.z CAR (SEQ ID NO: 12) persist in vivo when administered to mice inoculated with CD276$^+$ 143b sarcoma cells.

Figure 6A:
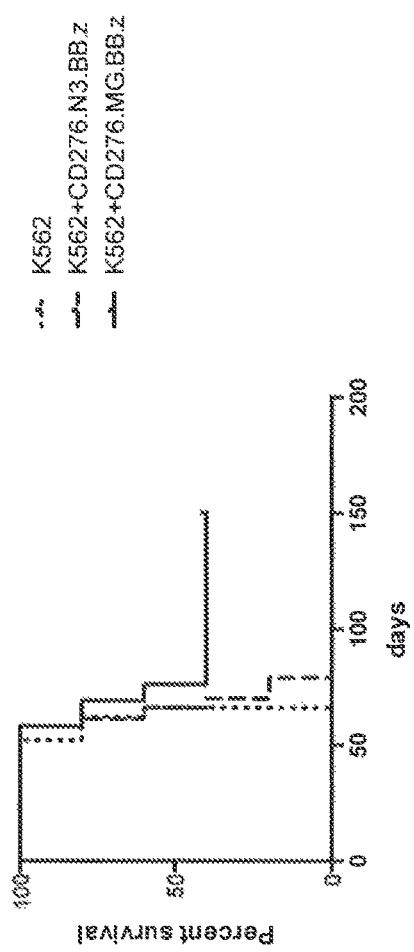
FIGS. 6A and 6B are graphs showing the percentage (%) of CAR+/CD3+ peripheral blood mononuclear cells (PBMC) 21 days (A) and 45 days (B) after mice were inoculated with tumor cells. Mice were treated with cells transduced with the CD276.MG.BB.z CAR (SEQ ID NO: 12), the CD276.N3.BB.z CAR, or an anti-CD19 CAR (CD19.BB.z) to mice. Untransduced T cells (1×10$^6$) (mock T cells) were administered to mice as a control.

Mice were inoculated with CD276$^+$ 143b sarcoma cells. Cells were transduced with the CD276.MG.BB.z CAR (SEQ ID NO: 12), the CD276.N3.BB.z CAR, or an anti-CD19 CAR. On Day 2 following inoculation, transduced cells (1×10$^6$) were administered to the mice. Untransduced T cells (1×10$^6$) (mock T cells) were administered to mice as a control. The percentage of CAR+/CD3+ cells was counted by flow cytometry on Days 21 and 45 after inoculation. The results are shown in FIGS. 6A and 6B.

Figure 6C:
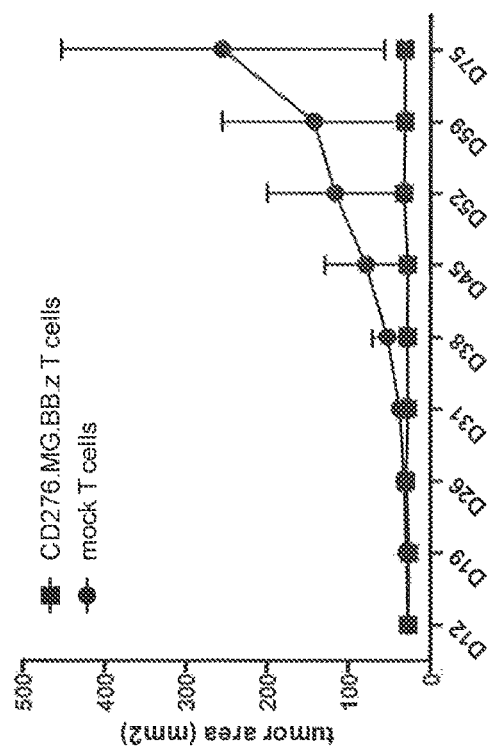
FIG. 6C is a graph showing the percentage of K562 tumor-bearing mice surviving at various time points (days) after administering K562 cells alone (dotted line), K562 cells followed by cells transduced with the CD276.MG.BB.z CAR (SEQ ID NO: 12) (solid line), or K562 cells followed by the CD276.N3.BB.z CAR (dashed line) to the mice.
Figure 6B:
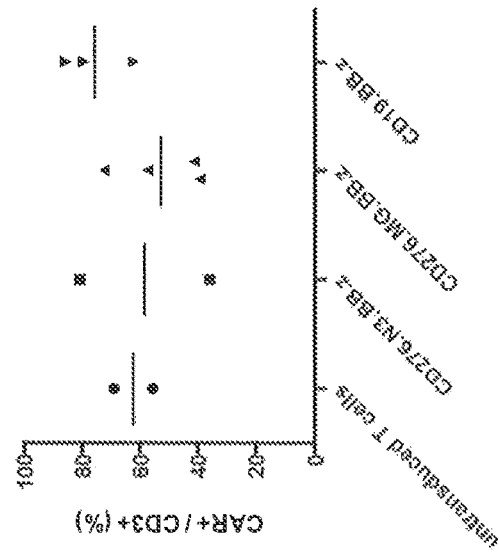

As shown in FIG. 6B, greater numbers of the cells that were transduced with the CD276.MG.BB.z CAR (SEQ ID NO: 12) persisted at Day 45 in vivo as compared to cells transduced with the CD276.N3.BB.z CAR or the anti-CD19 CAR.

Example 9

This example demonstrates that tumor-bearing mice treated with cells transduced with the CD276.MG.BB.z CAR (SEQ ID NO: 12) survived longer than mice treated with cells transduced with the CD276.N3.BB.z CAR.

Mice were injected intravenously (IV) with K562 cells (5×10$^6$) on Day 0. On Day 2 following injection of K562 cells, mice were treated with untransduced mock T cells, or T cells that were transduced with the CD276.MG.BB.z CAR (SEQ ID NO: 12) or the CD276.N3.BB.z CAR. The survival of the mice was monitored for up to 80 days after administration of the K562 cells. The results are shown in FIG. 6C.

As shown in FIG. 6C, K562 tumor-bearing mice treated with the cells transduced with the CD276.MG.BB.z CAR (SEQ ID NO: 12) survived longer than mice treated with the untransduced cells or the cells transduced with the CD276.N3.BB.z CAR.

Example 10

This example demonstrates that administration of cells transduced with the CD276.MG.BB.z CAR (SEQ ID NO: 12) to tumor-bearing mice decreases tumor size in vivo.

Figure 6D:
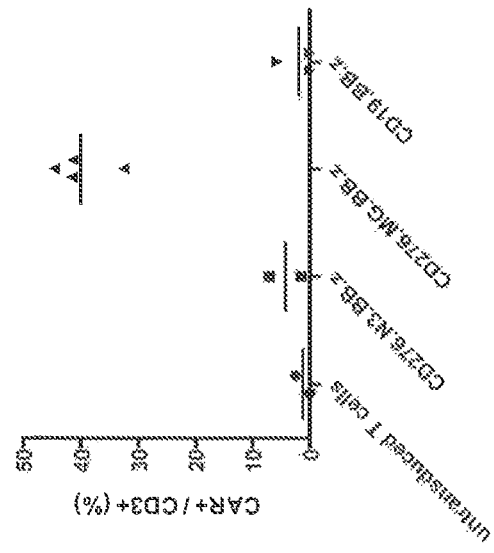
FIG. 6D is a graph showing the tumor size (mm$^2$) in mice treated with cells transduced with the CD276.MG.BB.z CAR (SEQ ID NO: 12) (squares) or mock-transduced cells (circles) at various time points (days) after inoculation with tumor cells.

Mice were orthotopically inoculated with CD276$^+$ osteosarcoma cells (1×10$^5$ MG63.3-GFP) on Day 0. The mice received cyclophosphamide 3 mg/mouse intraperitoneally (IP) on Day 3. Cells were transduced with the CD276.MG.BB.z CAR (SEQ ID NO: 12) or were untransduced. Mice were treated with transduced or untransduced cells (1×10$^6$) on Day 5. The mice were treated with recombinant human interleukin 7 three times weekly for three weeks. The size of the tumors was measured at various time points beginning on Day 12 up to Day 75 after inoculation. The results are shown in FIG. 6D. As shown in FIG. 6D, mice treated with the CD276.MG.BB.z CAR (SEQ ID NO: 12) appeared to be cured of the sarcoma, whereas all mice treated with the mock transduced cells succumbed to progressive tumor growth.

Example 11

This example demonstrates that administration of cells transduced with the CD276.MG.BB.z CAR (SEQ ID NO: 12) induces regression of established osteosarcoma in tumor-bearing mice.

Figure 7:
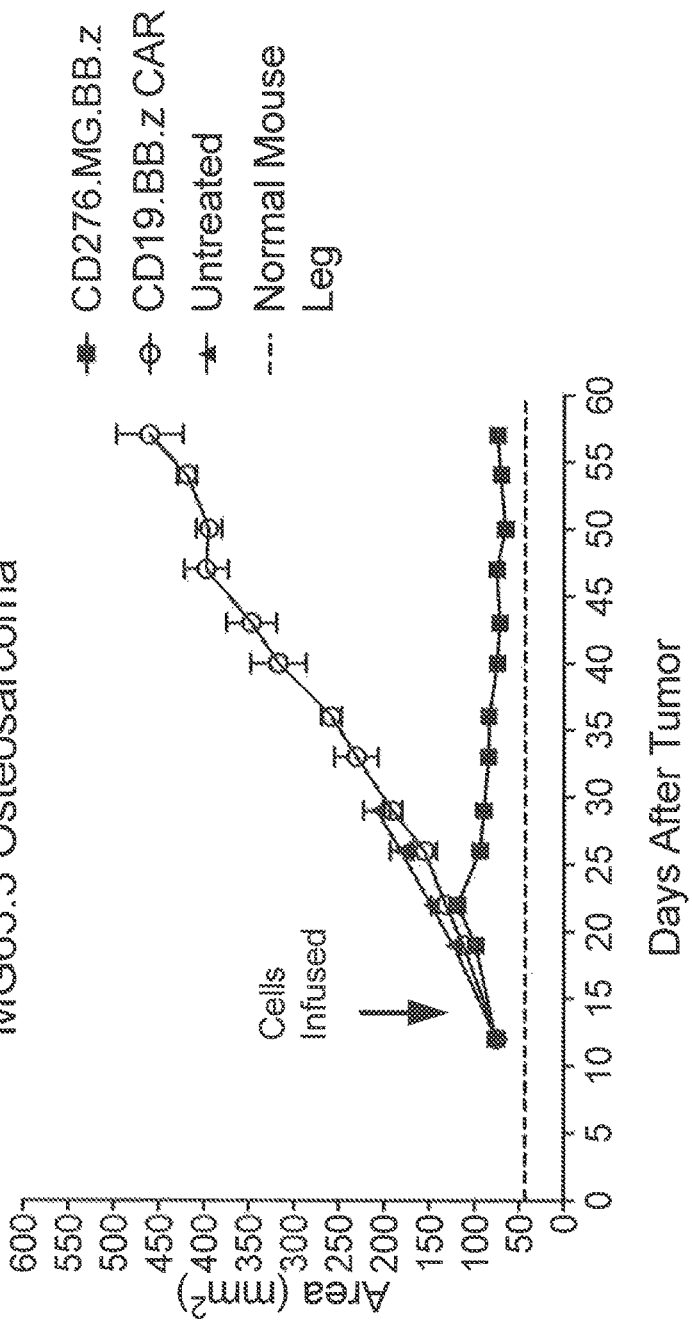
FIG. 7 is a graph showing the tumor size (mm$^2$) in untreated mice (triangles) or mice treated with cells transduced with the CD276.MG.BB.z CAR (SEQ ID NO: 12) (squares) or CD19.BB.z CAR (irrelevant CAR) (circles). CAR T cells were infused 14 days after inoculation with MG63.3 osteosarcoma.

Mice were orthotopically inoculated with CD276+ osteosarcoma cells (1×10$^5$ MG63.3-GFP) on Day 0. The tumor was allowed to grow for 14 days. No cytotoxic therapy was administered. Cells were transduced with the CD276.MG.BB.z CAR (SEQ ID NO: 12) or a control CD119.BB.z CAR. On Day 14 after tumor inoculation, 10×10$^6$ CD276.MG.BB.z CAR (SEQ ID NO: 12)-transduced cells or 10×10$^6$ CD19.BB.z CAR-transduced cells were infused intravenously. No cytokines were administered. The size of the tumors was measured at various time points beginning on Day 12 up to Day 60 after inoculation. The results are shown in FIG. 7. As shown in FIG. 7, mice treated with the CD276.MG.BB.z CAR (SEQ ID NO: 12)-transduced cells demonstrated tumor regression and long-term control of the sarcoma, whereas all mice treated with CD19.BB.z-CAR (irrelevant CAR) transduced cells succumbed to progressive tumor growth.

Example 12

This example demonstrates that administration of cells transduced with the CD276.MG.BB.z CAR (SEQ ID NO: 12) induces regression of established medulloblastoma, an aggressive brain tumor, in mice.

Figure 8:
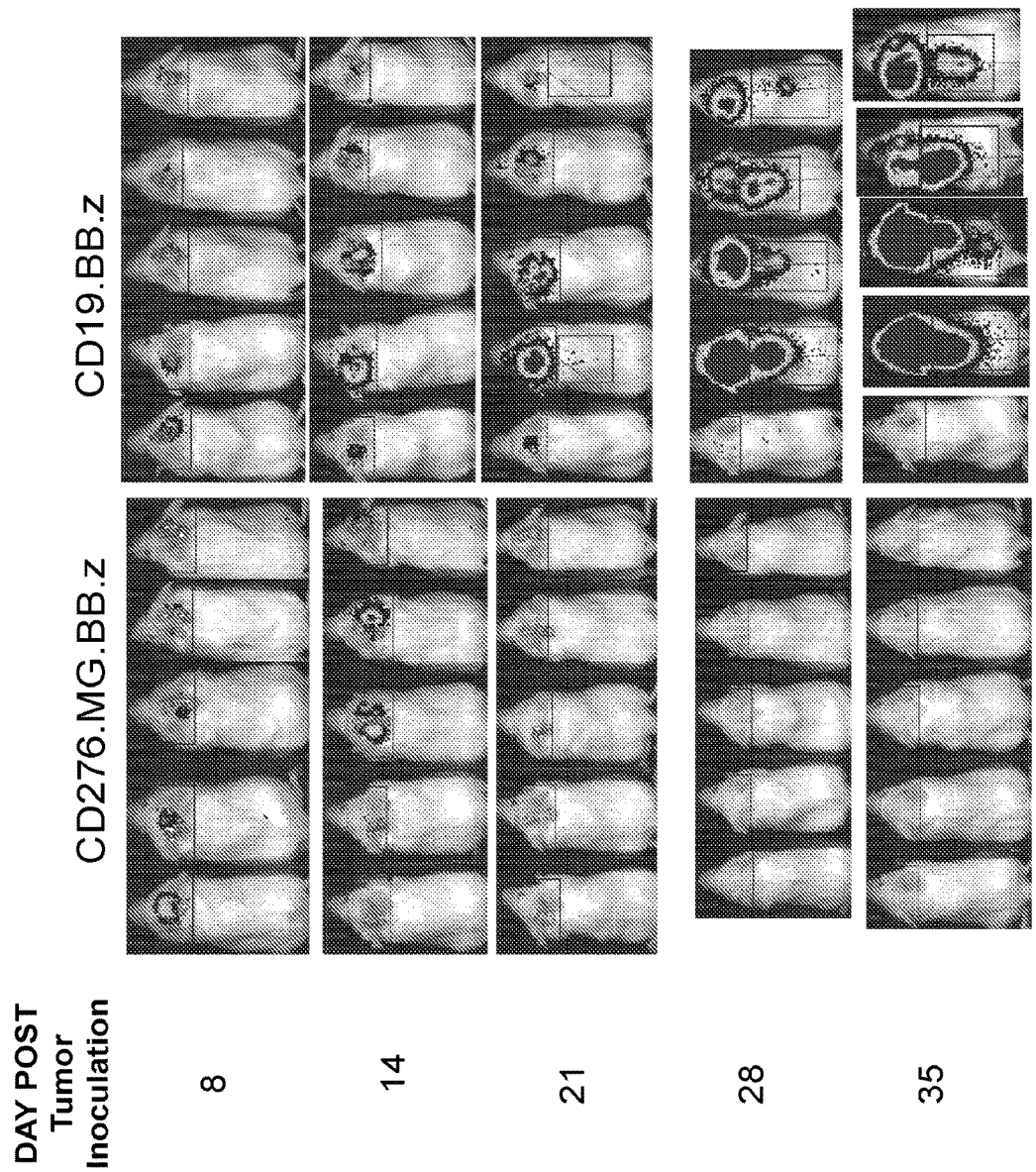
FIG. 8 shows sequential images of immunodeficient NSG mice inoculated with bioluminescent DAOY-GFP-luciferase+ medulloblastoma into the cerebellum. Eight days after tumor inoculation, animals received intravenous injections of CD276.MG.BB.z (SEQ ID NO: 12) (left) or CD19.BB.z CAR (irrelevant CAR) (right)-transduced T cells. Tumors continued to grow in animals receiving CD19.BB.z CAR T cells but regressed in animals given CD276.MG.BB.z (SEQ ID NO: 12) T cells.

Mice were orthotopically inoculated with CD276+ DAOY medulloblastoma cells ($5\times10^5$ DAOY-GFP-luc) which express luciferase, an enzyme that allows the tumor to be visualized sequentially upon anesthesia of the tumor-bearing mice. Tumors were allowed to grow for 8 days, at which time the growing tumor could be visualized in the cerebellum. On Day 8 after tumor inoculation, $10\times10^6$ CD276.MG.BB.z CAR (SEQ ID NO: 12)-transduced cells or control $10\times10^6$ CD19.BB.z CAR-transduced cells were infused intravenously. No cytotoxic therapy or cytokines were administered. Tumor growth was monitored by bioluminescence through Day 35. The results are shown in FIG. 8. As shown in FIG. 8, mice treated with the CD276.MG.BB.z CAR (SEQ ID NO: 12) underwent tumor regression and long term disease control of the medulloblastoma, whereas all mice treated with CD19.BB.z-CAR (irrelevant CAR) transduced cells succumbed to progressive tumor growth.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) comprising the amino acid sequence of SEQ ID NO: 12.

2. A nucleic acid comprising a nucleotide sequence encoding the CAR of claim 1.

3. A recombinant expression vector comprising the nucleic acid of claim 2.

4. A pharmaceutical composition comprising the CAR according to claim 1 and a pharmaceutically acceptable carrier.

5. A method of detecting the presence of cancer in a mammal, the method comprising: (a) contacting a sample comprising one or more cells from the mammal with the CAR according to claim 1, thereby forming a complex, and (b) detecting the complex, wherein detection of the complex is indicative of the presence of cancer in the mammal, wherein the cancer expresses cluster of differentiation 276 (CD276).

6. The method according to claim 5, wherein the cancer is a solid tumor, carcinoma, neuroblastoma, Ewing's sarcoma, rhabdomyosarcoma, prostate cancer, ovarian cancer, colorectal cancer, or lung cancer.

7. A method of treating or preventing cancer in a mammal, the method comprising administering to the mammal the CAR according to claim 1 in an amount effective to treat or prevent cancer in the mammal, wherein the cancer expresses cluster of differentiation 276 (CD276).

8. The method according to claim 7, wherein the cancer is a solid tumor, carcinoma, neuroblastoma, Ewing's sarcoma, rhabdomyosarcoma, prostate cancer, ovarian cancer, colorectal cancer, or lung cancer.

* * * * *